(12) United States Patent
Diel

(10) Patent No.: US 9,611,454 B2
(45) Date of Patent: Apr. 4, 2017

(54) SYSTEM AND METHOD FOR CELL SEPARATION

(71) Applicant: Sartorius Stedim Biotech GmbH, Goettingen (DE)

(72) Inventor: Bernhard Diel, Dransfeld (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 523 days.

(21) Appl. No.: 14/358,499

(22) PCT Filed: Oct. 10, 2012

(86) PCT No.: PCT/EP2012/004236
§ 371 (c)(1),
(2) Date: May 15, 2014

(87) PCT Pub. No.: WO2013/079136
PCT Pub. Date: Jun. 6, 2013

(65) Prior Publication Data
US 2016/0348061 A1    Dec. 1, 2016

(30) Foreign Application Priority Data
Dec. 1, 2011    (DE) .................. 10 2011 119 816

(51) Int. Cl.
*C02F 1/42*    (2006.01)
*C12M 1/00*    (2006.01)
(Continued)

(52) U.S. Cl.
CPC ............ *C12M 47/04* (2013.01); *C12M 23/14* (2013.01); *C12M 23/28* (2013.01); *C12M 27/02* (2013.01); *C12M 29/04* (2013.01); *C12M 37/02* (2013.01)

(58) Field of Classification Search
None
See application file for complete search history.

(56) References Cited

U.S. PATENT DOCUMENTS 2,455,130 A    11/1948    Lomax
6,596,521 B1    7/2003    Chang et al.
(Continued)

FOREIGN PATENT DOCUMENTS

DE    195 37 874    4/1997
DE    100 17 256    2/2001
(Continued)

OTHER PUBLICATIONS

English Translation of International Preliminary Report on Patent Ability—Jun. 12, 2014 English Translation of Written Opinion.
(Continued)

*Primary Examiner* — Chester Barry
(74) *Attorney, Agent, or Firm* — Gerald E. Hespos; Michael J. Porco; Matthew T. Hespos

(57) ABSTRACT

The invention relates to a system and a method for cell separation via a filter, with a powder bag which can be arranged in a recirculation circuit and is partly filled with a pulverulent filter aid and to which a cell solution containing the cells to be separated can be delivered from a bioreactor via a pump arranged in the recirculation circuit, the bioreactor, which has an agitator, being arranged in the recirculation circuit, and, when the recirculation circuit is interrupted, the bioreactor being connectable to the filter.

11 Claims, 7 Drawing Sheets

(51) Int. Cl.
   *C12M 1/06*      (2006.01)
   *C12M 1/12*      (2006.01)

(56) References Cited

U.S. PATENT DOCUMENTS

2004/0245124 A1* 12/2004 Hurst .................... B01F 5/106
                                                      206/219
2011/0318814 A1   12/2011 Kshirsagar et al.

FOREIGN PATENT DOCUMENTS

WO      00/24918      5/2000
WO      2010/078404   7/2010

OTHER PUBLICATIONS

International Search Report of Jan. 4, 2013.

* cited by examiner

SYSTEM AND METHOD FOR CELL SEPARATION

BACKGROUND

1. Field of the Invention

The invention relates to a system for cell separation via a filter, with a powder bag which can be arranged in a recirculation circuit and is partly filled with a pulverulent filter aid and to which cell solution containing the cells to be separated can be delivered from a bioreactor via a pump arranged in the recirculation circuit.

2. Description of the Related Art

The invention relates, furthermore, to a method for cell separation via a filter, with a powder bag which is arranged in a recirculation circuit and is partly filled with a pulverulent filter aid and to which a cell solution containing the cells to be separated is delivered from a bioreactor via a pump arranged in the recirculation circuit.

For precoating filtration, a pulverulent filter aid is used, which is also known in the filtration industry by the synonyms of kieselguhr/silica/diatomaceous earth or diatoms. This filter aid has the property of forming, together with the particulate constituents which are to be separated from a liquid, on a carrier material (for example, a filter web), a precoat cake which is distinguished by especially high porosity and makes it possible to have a high filter capacity.

The filter aid, in powder form, entails some risks in handling and accordingly has to be handled safely, as, for example, in the handling of powders based on silicon dioxide (for example, quartz-containing dusts), in which there is the risk of silicosis when respirable particles are inhaled. In this context, the use of disposable products has proved to be especially advantageous in biotechnology. Where disposable products are concerned, it is advantageous if these have no metal and if they are formed relatively simply and cost-effectively.

US 2004/0245124 A1 discloses a system and a method for cell separation via a filter by means of precoating filtration. In this case, a cell solution from a bioreactor is delivered, via a pump arranged in a recirculation circuit, to a powder or mixing container which is arranged in a recirculation circuit and is partly filled with a pulverulent filter aid.

The disadvantage of this is that the bioreactor is arranged outside the recirculation circuit and the powder bag has to accommodate the entire cell solution or cell liquor of the bioreactor in addition to the filter aid. This is difficult to handle and is relatively costly. Furthermore, a second pump preceding the filter is required for filtration.

The object of the present invention is, therefore, to provide a system for cell separation by precoating filtration, which is safe, avoids contaminating the surroundings, can be handled simply and is also suitable for cost-effective use of its relevant parts as a disposable product.

A further object of the present invention is to specify a method for cell separation by precoating filtration by means of a corresponding system, which is safe, avoids contaminating the surroundings, can be handled simply and is also cost-effective.

SUMMARY OF THE INVENTION

The invention relates to a system for cell separation via a filter. The system has a powder bag that can be arranged in a recirculation circuit and that is filled partly with a pulverulent filter aid. The cell solution can be delivered from a bioreactor to the powder via a pump in the recirculation circuit. The bioreactor has an agitator and is arranged. If the recirculation circuit is interrupted, the bioreactor is connectable to the filter.

By the bioreactor, together with the powder bag, being arranged in the recirculation circuit, there is no need for the entire bioreactor liquid to be recirculated in order to produce the suspension, but instead only a small liquid stream is routed via the powder bag having the filter aid. The powder bag is both a transport and a mixing bag and does not require the volume of the bioreactor. The powder bag is smaller and can therefore be handled more easily. Moreover, a plurality of small bags with small easy-to-handle kieselguhr quantities of 10-15 kg may be used as filter aids. One or more small part quantities of equal size may, depending on the reactor size and metering quantity, be connected and suspended in succession, that is to say the quantity of filter aid or the kieselguhr quantity may be varied immediately prior to filtration.

The recirculation of this small quantity takes place only until the suspension in the powder bag is pumpable. The suspension is thereafter held in suspense in the bioreactor by means of a gentle agitator. The process is consequently more careful and minimizes the undesirable influences caused by the destruction of cells.

According to a preferred embodiment of the invention, the bioreactor has on top in the vertical direction a first reactor hose which is connectable via a first connector to a first powder bag hose arranged on top of the powder bag in the vertical direction. Furthermore, the bioreactor has at the bottom in the vertical direction a second reactor hose which is connectable via a second connector to a second powder bag hose arranged at the bottom of the powder bag in the vertical direction. The powder bags can be connected relatively simply and quickly via the connectors to the bioreactor to form the recirculation circuit. It is consequently also possible, for example, to deliver the powder bags, together with the powder bag hoses and connectors, as presterilized units.

According to a further preferred embodiment of the invention, the first powder bag hose has, preceding the first connector toward the powder bag, a first valve, and the second powder bag hose has, preceding the second connector toward the powder bag, a second valve. The second reactor hose has, preceding the second connector toward the bioreactor, a third valve.

This ensures that contamination of the surroundings is avoided after the removal of the powder bag. The powder bag can be removed or exchanged together with its powder bag hoses and valves.

According to a further preferred embodiment of the invention, the pump, which is designed as a peristaltic pump, is arranged between the third valve and the bioreactor. The arrangement makes it unnecessary to have a further pump for the subsequent filtration step. The design as a peristaltic or hose pump has the effect that it can be reused, since, in particular, it does not come into contact with the media.

According to a further preferred embodiment of the invention, with the powder bag removed, the filter is connectable via a third connector to the connector-side end of the second reactor hose.

The cell solution located in the bioreactor together with the suspended filter aid can thereby be delivered simply and reliably via the pump to the filter for precoating filtration.

According to a further preferred embodiment of the invention, the bioreactor together with the reactor hoses, the powder bag together with the powder bag hoses and the filter are designed as disposable parts. Moreover, as a result of the cost-effective form of the disposable parts, safety in avoiding undesirable contamination of the environment, for example due to contamination by toxic dusts in the event of the undesirable release of the filter aid, is further increased.

The invention also relates to a method that may use the above-described system for cell separation. The method includes connecting the bioreactor in the recirculation circuit to the powder bag. The method then includes recirculating the cell solution that is conveyed out of the bioreactor into the powder bag. After sufficient suspension of the filter aid, the method includes reversing the conveying direction of the pump. The method then includes emptying or exchanging the powder bag. The method further includes connecting the filter to the bioreactor via a connector, and subjecting a suspension composed of cell solution and of filter aid from the bioreactor to filtration by means of the filter.

By virtue of the bioreactor together with the powder bag being arranged in the recirculation circuit, there is no need for the entire bioreactor liquid to be recirculated in order to produce the suspension, but instead only a small liquid stream is routed via the powder bag having the filter aid. The powder bag is both a transport and a mixing bag and does not require the volume of the bioreactor. The powder bag is smaller and can therefore be handled more easily. Moreover, a plurality of small bags with small easy-to-handle kieselguhr quantities of, for example, 10-15 kg may be used as filter aids.

The recirculation of this small quantity takes place only until the suspension in the powder bag is pumpable. The suspension is thereafter held in suspense in the bioreactor by means of a gentle agitator. The process is consequently more careful and minimizes the undesirable influences caused by the destruction of cells. On the one hand, the connection between the filter and bioreactor may take place, with the powder bag removed, and, on the other hand, it is also possible to connect the filter to the bioreactor via a branch and a further valve. It is important that, after the powder bag is emptied, its adjacent valves are closed and the recirculation circuit is interrupted.

According to a further preferred embodiment of the invention, depending on the required quantity of filter aid, further powder bags are used in exchange before filtration and their suspended powder is delivered to the bioreactor.

Thus, one or more small part quantities of equal size may, depending on the reactor size and the metering quantity, be connected and suspended in succession. That is to say, the quantity of filter aid or the kieselguhr quantity may be varied immediately prior to filtration.

Further particulars of the invention may be gathered from the following detailed description and the accompanying drawings in which preferred embodiments of the invention are illustrated by way of example.

DETAILED DESCRIPTION OF THE PREFERRED EMBODIMENTS

Figure 1:
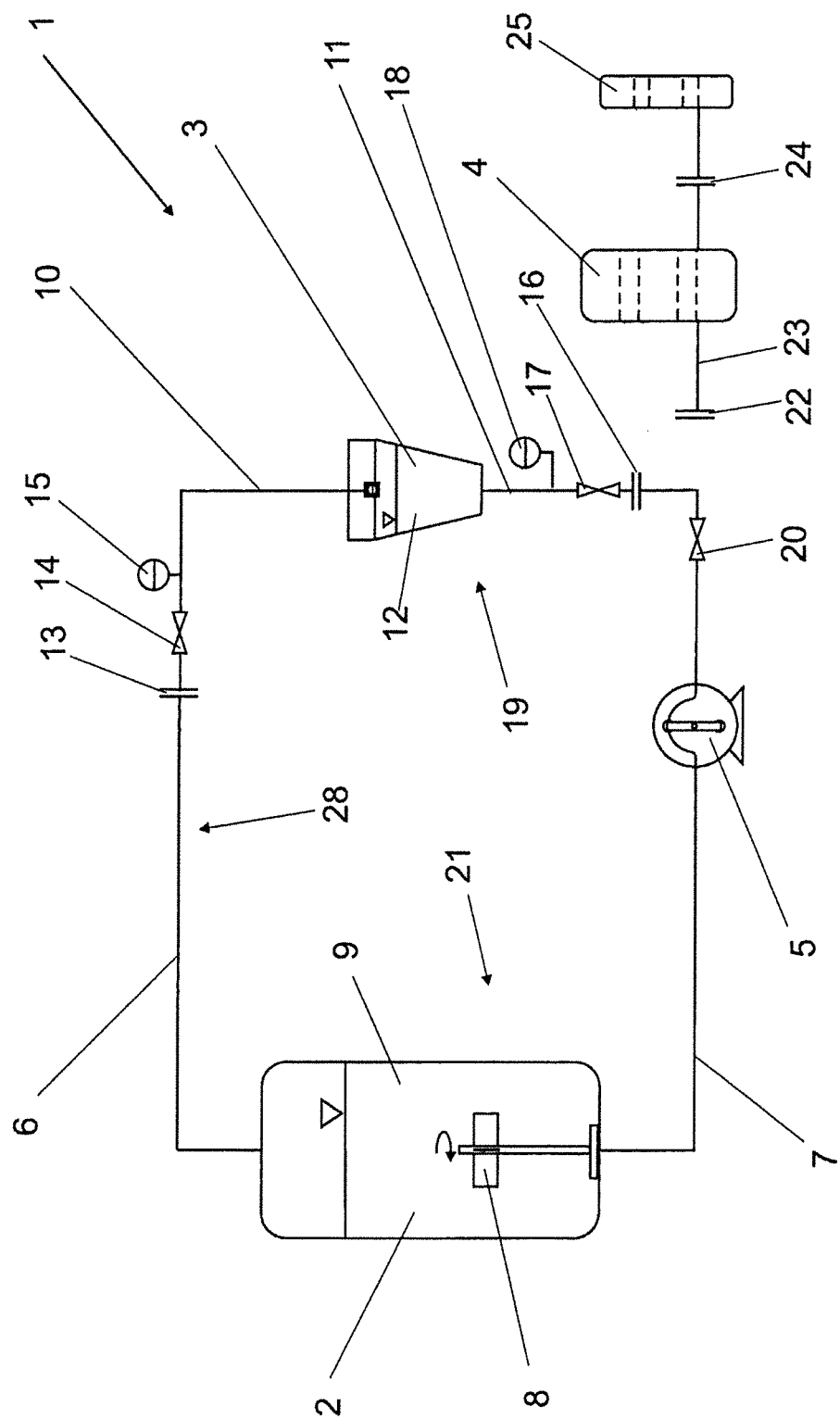
FIG. 1 shows a system for cell separation, with an installed powder bag in the recirculation circuit, with the first and the second valve closed and with the filter separated.
Figure 2:
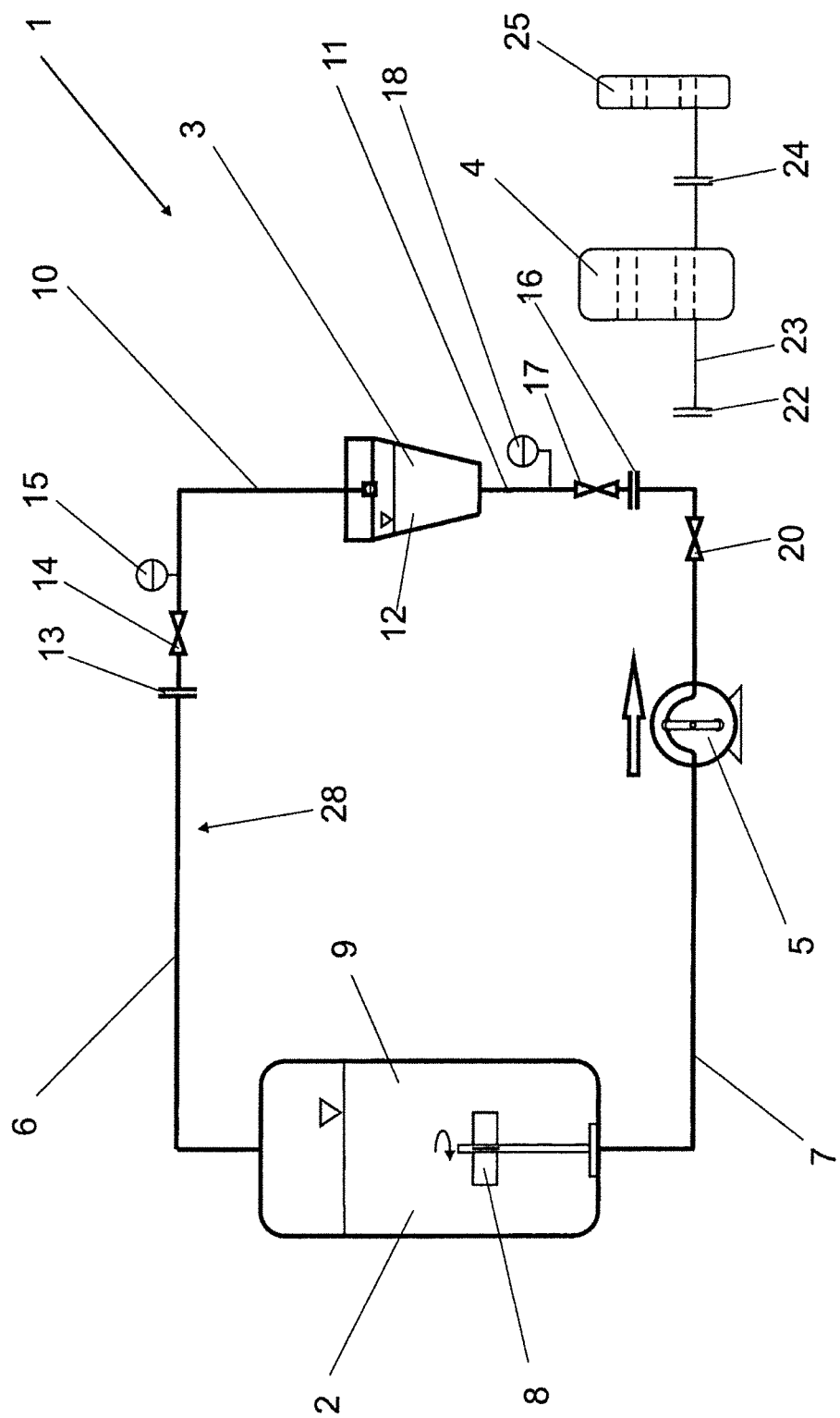
FIG. 2 shows the system of FIG. 1, with the valves open and with the conveyance of cell solution via a pump into the dry powder bag.
Figure 3:
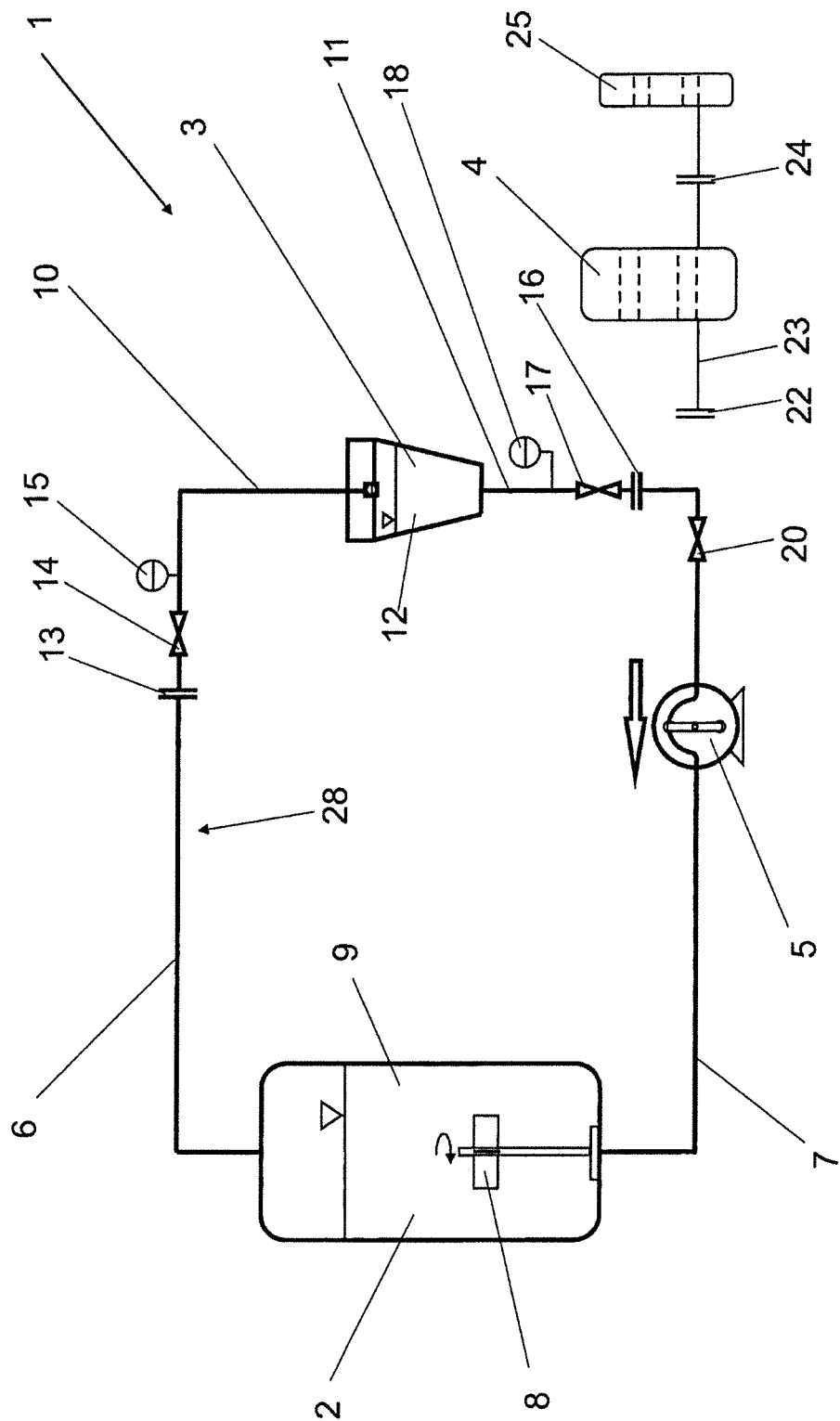
FIG. 3 shows the system of FIG. 2 with the conveyance of filter aid suspended in cell solution out of the powder bag into the bioreactor with reversed conveying direction of the pump.
Figure 4:
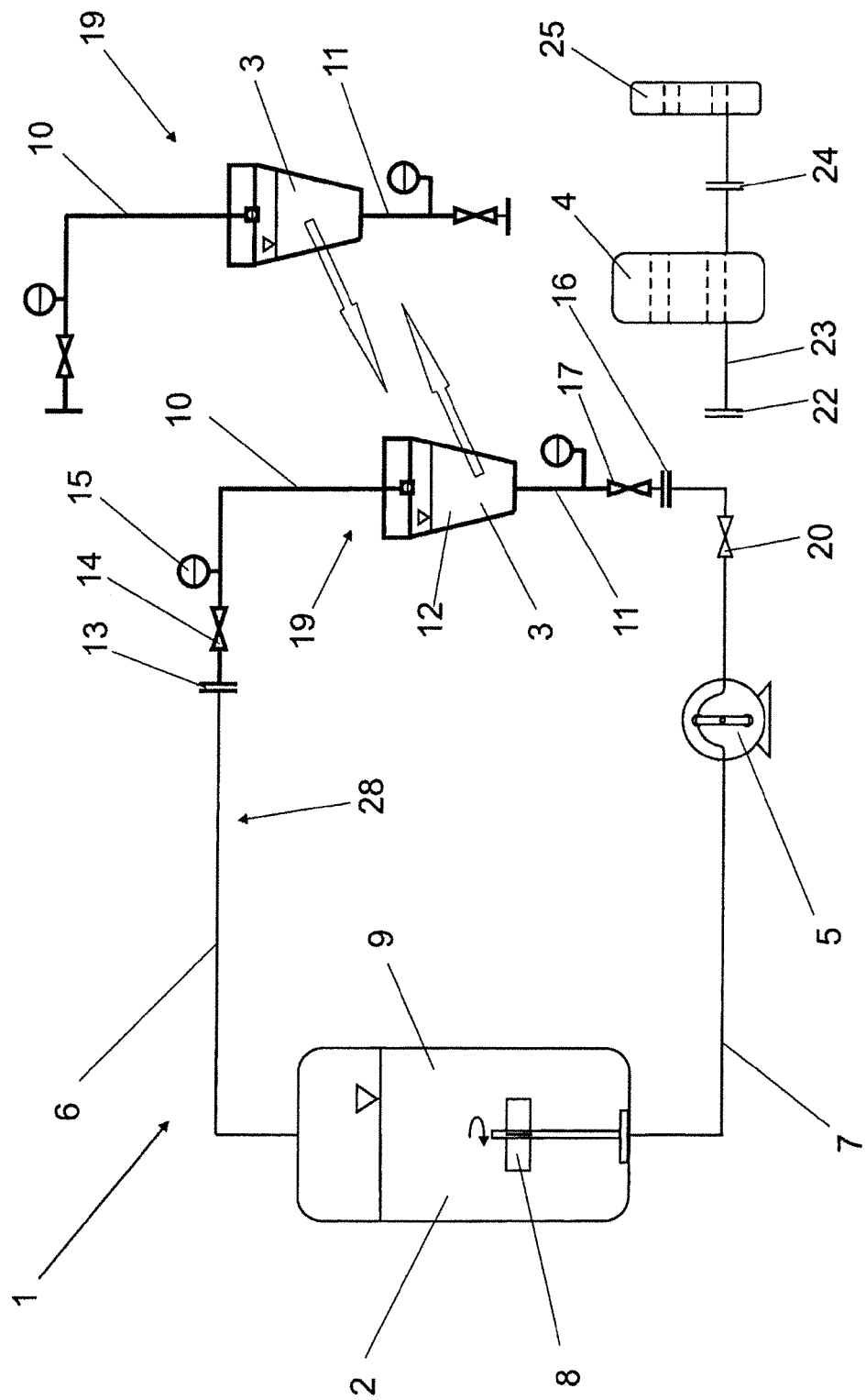
FIG. 4 shows the system of FIG. 3 with the valves closed and with a second powder bag to be exchanged and having powder bag hoses, valves, pressure sensors and connector parts.
Figure 5:
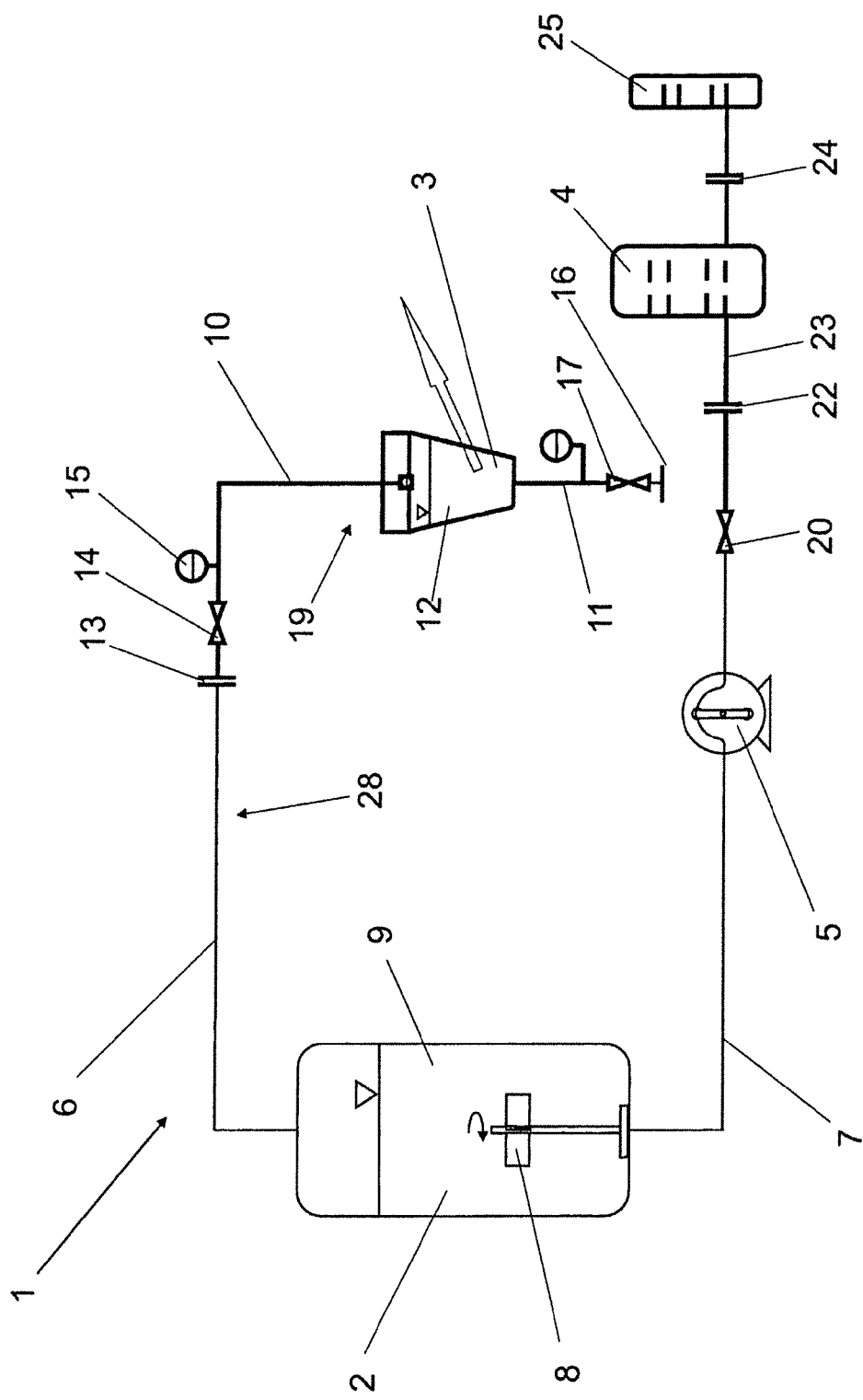
FIG. 5 shows the system of FIG. 4 with the valves closed, with the connector connection between the second powder bag hose and second reactor hose released, and with the connection of the second reactor hose via a third connector connection to a feed hose to the filter for precoating filtration.
Figure 6:
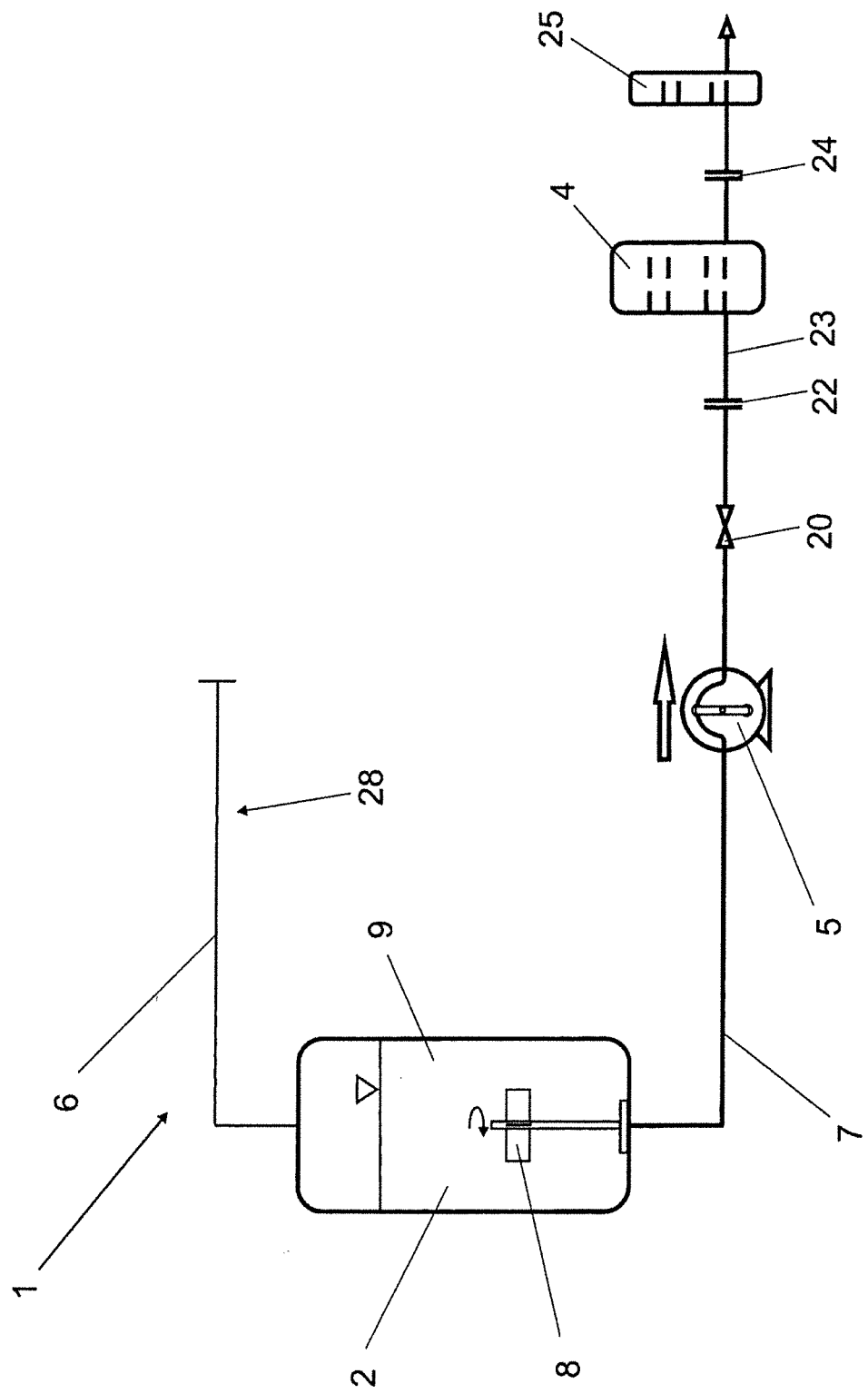
FIG. 6 shows the system of FIG. 5 with the valves open and with the conveyance of cell solution together with suspended filter aid to the filter via the pump.

A system 1 for cell separation by precoating filtration is composed essentially of a bioreactor 2, of a powder bag 3, of a filter 4 and of a pump 5.

The bioreactor 2 has a first reactor hose 6 at its upper end in the vertical direction and a second reactor hose 7 at its lower end in the vertical direction. An agitator 8 is arranged in a known way in the inner space of the bioreactor 2. The bioreactor 2 has a cell solution 9 containing cells to be separated.

The powder bag 3 has a first powder bag hose 10 on top in the vertical direction. A second powder bag hose 11 is arranged on the powder bag 3 at the bottom in the vertical direction. Upon delivery, the powder bag 3 contains a dry pulverulent filter aid 12 which is required for precoating filtration in the filter 4.

The first reactor hose 6 and the first powder bag hose 10 are connected to one another via a first connector 13 which is designed, for example, as a two-part sterile connector. The first powder bag hose 10 has a first valve 14 between the first connector 13 and the powder bag 3. A first pressure sensor 15 is arranged between the first valve 14 and the powder bag 3. The second reactor hose 7 is connected to the second powder bag hose 11 via a second connector 16. The second powder bag hose 11 has a second valve 17 between the second connector 16 and the powder bag 3. A second pressure sensor 18 is arranged between the second valve 17 and the powder bag 3. The powder bag 3, together with the powder bag hoses 10, 11, with the valves 14, 17, with the pressure sensors 15, 18 and with connector connections 13, 16, forms an exchangeable powder bag set 19 which is capable of being delivered, sterile, and which is formed from disposable parts and is therefore suitable for once-only use (single use).

The second reactor hose 7 has a third valve 20 between the second connector 16 and the bioreactor 2. The pump 5 is arranged between the third valve 20 and the bioreactor 2. The pump 5 is designed, for example, as a peristaltic pump which may be a hose pump.

The bioreactor 2, together with its agitator 8 and the reactor hoses 6, 7, with the third valve 20 and with the connector parts 13, 16, may form a reactor set 21 which is likewise formed from disposable parts and is suitable for once-only use (single use). The reactor set 21 may also be delivered, sterile.

According to the embodiments of FIGS. 1 to 6, after the removal of the powder bag set 19 the filter 4 is connected to the second reactor hose 7 via a third connector 22 which is connected to the filter 4 via a filter hose 23. The filter 4 may be followed by a fourth connector 24 by a layered or sterile filter 25.

The filters 4 and 25 may also be formed as disposable parts.

Figure 7:
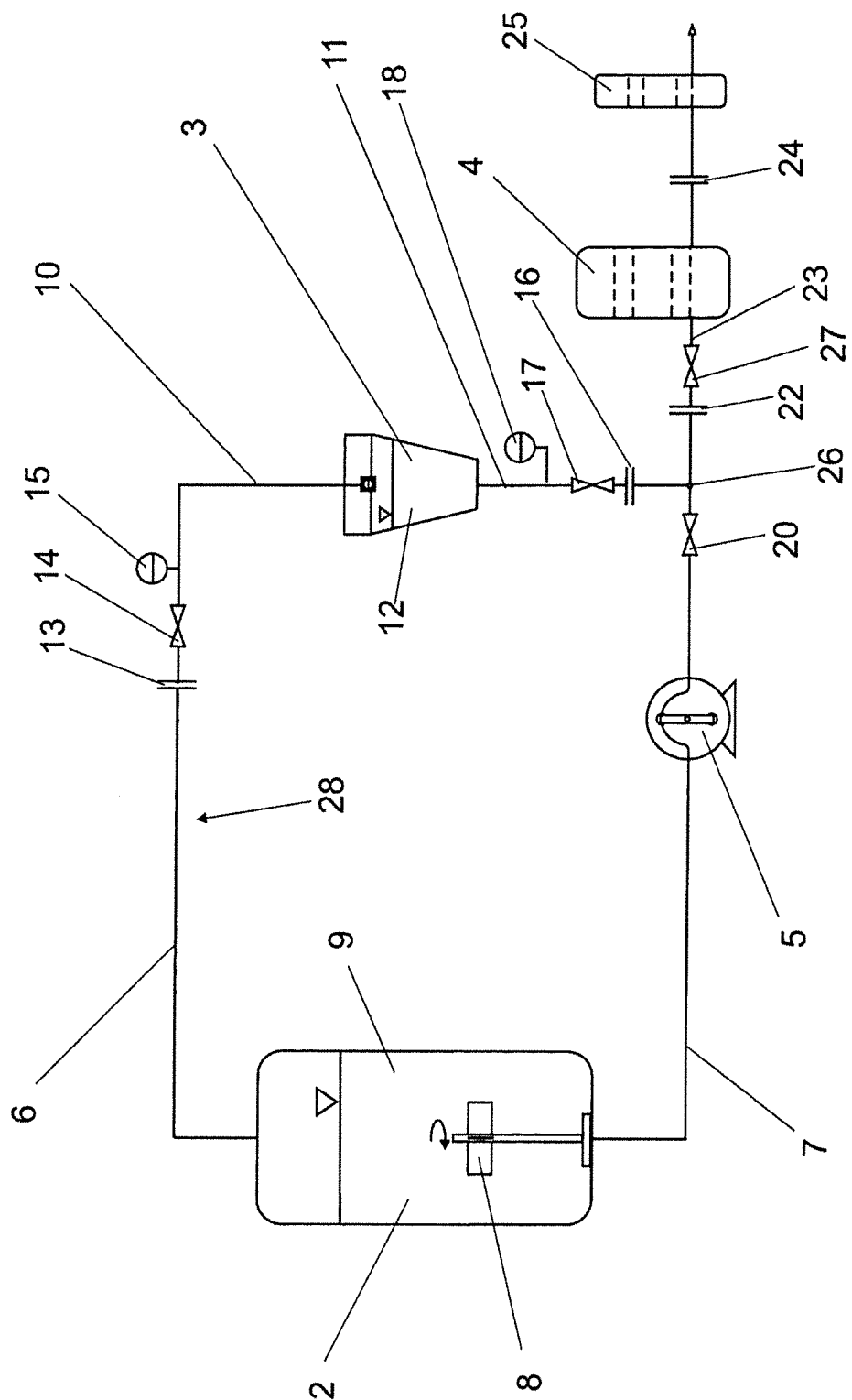
FIG. 7 shows a further system for cell separation with an installed powder bag in the recirculation circuit and with a filter connected via a branch and an additional valve.

According to the exemplary embodiment of FIG. 7, the filter 4 may also be connected to the second powder bag hose 11 via a branch part 26. In this case, a fourth valve 27 is arranged in the filter hose 23 between the third connector 22 and the filter 4.

The method for cell separation may be carried out by means of the following process steps:

1) Installation of the powder bag 3 and production of a recirculation circuit 28 by the connection of the first powder bag hose 10 to the first reactor hose 6 via the first connector 13 and by the connection of the second powder bag hose 11 to the second reactor hose 7 via the second connector 16.

2) Opening of the valves 14, 17, 20, starting of the pump 5 and conveyance of cell solution 9 out of the bioreactor 2 into the dry powder bag 3, so that the cell solution 9 rises in the powder bag 3 and wets and (partly) suspends the filter aid 12, the inlet and outlet pressure at the powder bag 3 being monitored via the pressure sensors 15, 18 and, if appropriate, being corrected. After a recirculation time, the filter aid 12 is sufficiently suspended in the cell solution 9 and is therefore pumpable, so that the pump 5 is stopped.

3) The pump is started in the opposite conveying direction, and the pumpable suspension of cell solution 9 and of filter aid 12 is conveyed completely out of the powder bag 3 into the bioreactor 2. At the same time, the powder bag 3 is emptied and is contracted by suction. After the compete emptying of the powder bag 3, the pump 5 is stopped.

4) The valves 14, 17, 20 are closed and the powder bag set 19 is separated at the connectors 13, 16 and, if appropriate, exchanged for a new powder bag set 19.

Steps 1 to 3 are repeated until the entire quantity of filter aid 12 provided is suspended and is introduced into the bioreactor 2.

5) The last powder bag set 19 is then released at the connectors 13, 16 and removed after the closing of the valves 14, 17, 20. The second reactor hose 7 is subsequently connected to the filter 4 via the third connector 22. Alternatively, after the closing of the valve 17, the filter 4 may also be connected to the branch part 26 and therefore to the second reactor hose 7 via the fourth valve 27 and the third connector 22.

6) The pump 5 is started with a conveying direction toward the filter 4, and the cell solution 9, together with suspended filter aid 12, is conveyed out of the bioreactor 2 through the filters 4, 25.

What is especially suitable for carrying out the method according to the invention is a powder bag 3, of which the end pointing vertically downward and connected to the second powder bag hose 11 is funnel-shaped or tapered conically and which is connectable to an external shaking device, not shown, which acts upon the exterior of the powder bag 3 in order to bring about effective suspension of the filter aid 12 in the cell solution 9 located in the powder bag 3.

LIST OF REFERENCE SYMBOLS

1 System
2 Bioreactor
3 Powder bag
4 Filter
5 Pump
6 First reactor hose of 2
7 Second reactor hose of 2
8 Agitator of 2
9 Cell solution
10 First powder bag hose of 3
11 Second powder bag hose of 3
12 Filter aid
13 First connector
14 First valve
15 First pressure sensor of 10
16 Second connector
17 Second valve
18 Second pressure sensor of 11
19 Powder bag set
20 Third valve
21 Reactor set
22 Third connector
23 Filter hose of 4
24 Fourth connector
25 Sterile filter
26 Branch part
27 Fourth valve
28 Recirculation circuit

The invention claimed is:

1. A system (1) for cell separation via a filter (4), with a powder bag (3) which can be arranged in a recirculation circuit (28) and is partly filled with a pulverulent filter aid (12) and to which a cell solution (9) containing the cells to be separated can be delivered from a bioreactor (2) via a pump (5) arranged in the recirculation circuit (28), the bioreactor (2) having an agitator and being arranged in the recirculation circuit (28), wherein the bioreactor (2) is connectable to the filter (4) when the recirculation circuit is interrupted.

2. The system of claim 1, wherein the bioreactor (2) has on top in a vertical direction a first reactor hose (6) that is connectable via a first connector (13) to a first powder bag hose (10) arranged on top of the powder bag (3) in the vertical direction, and wherein the bioreactor (2) has at a bottom in the vertical direction a second reactor hose (7) that is connectable via a second connector (16) to a second powder bag hose (11) arranged on the powder bag (3) at the bottom in the vertical direction.

3. The system of claim 2, wherein the first powder bag hose (10) has, preceding the first connector (13) toward the powder bag (3), a first valve (14), the second powder bag hose (11) has, preceding the second connector (16) toward the powder bag (3), a second valve (17), and the second reactor hose (7) has, preceding the second connector (16) toward the bioreactor (2), a third valve (20).

4. The system of claim 3, wherein the pump (5) is arranged between the third valve (20) and the bioreactor (2).

5. The system of claim 4, wherein the pump (5) is a peristaltic pump.

6. The system of claim 3, wherein the powder bag (3), together with its powder bag hoses (10, 11) and with valves (14, 17), is removable or exchangeable.

7. The system of claim 3, wherein the filter (4) is connectable via a third connector (22) to a connector-side end of the second reactor hose (7).

8. The system of claim 1, wherein the bioreactor (2) together with the reactor hoses (6, 7), the powder bag (3) together with the powder bag hoses (10, 11) and the filter (4) are disposable.

9. A method for cell separation via a filter (4), comprising: providing a recirculation circuit (28) with a powder bag (3) partly filled with a pulverulent filter aid (12), a bioreactor (2)

and a pump (5); using the pump (5) to convey a cell solution (9) containing the cells to be separated from the bioreactor (2) cell solution (9) into the powder bag (3); recirculating the cell solution (9); reversing the conveying direction of the pump (5) after sufficient suspension of the filter aid (12); emptying or exchanging the powder bag (3); and subjecting a suspension composed of the cell solution (9) and the filter aid (12) from the bioreactor (2) to filtration by means of the filter (4) that is connected to bioreactor (2) via a connector (13, 16, 22).

10. The method of claim 9, wherein, depending on the required quantity of filter aid (12), further powder bags (3) are used in exchange before filtration and their suspended powder is delivered to the bioreactor (2).

11. The method of claim 9, further comprising using an agitator (8) to hold the filter aid (12) suspension in the bioreactor (2).

* * * * *